(12) United States Patent
Anand et al.

(10) Patent No.: US 10,304,226 B2
(45) Date of Patent: May 28, 2019

(54) ULTRASOUND FOCAL ZONE SYSTEM AND METHOD

(71) Applicants: B-K Medical Aps, Herlev (DK); Carestream Health Inc., Rochester, NY (US)

(72) Inventors: Ajay Anand, Rochester, NY (US); Mary B. Kyryk, Rochester, NY (US); Bo Martins, Rodovre (DK)

(73) Assignee: B-K Medical Aps, Herlev (DK)

( * ) Notice: Subject to any disclaimer, the term of this patent is extended or adjusted under 35 U.S.C. 154(b) by 85 days.

(21) Appl. No.: 15/222,277

(22) Filed: Jul. 28, 2016

(65) Prior Publication Data

US 2017/0032557 A1    Feb. 2, 2017

Related U.S. Application Data

(60) Provisional application No. 62/198,345, filed on Jul. 29, 2015.

(51) Int. Cl.
| | |
|---|---|
| *G06T 11/60* | (2006.01) |
| *A61B 8/00* | (2006.01) |
| *A61B 8/08* | (2006.01) |
| *G09G 5/377* | (2006.01) |

(52) U.S. Cl.
CPC ............ *G06T 11/60* (2013.01); *A61B 8/4488* (2013.01); *A61B 8/463* (2013.01); *G09G 5/377* (2013.01); *A61B 8/5207* (2013.01); *G06T 2210/41* (2013.01); *G09G 2340/12* (2013.01); *G09G 2354/00* (2013.01)

(58) Field of Classification Search
CPC .................................. G06T 11/60; A61B 8/00
USPC .......................................................... 345/634
See application file for complete search history.

(56) References Cited

U.S. PATENT DOCUMENTS

| | | | |
|---|---|---|---|
| 5,370,120 A | 12/1994 | Oppelt | |
| 6,705,995 B1 | 3/2004 | Poland | |
| 6,951,543 B2 | 10/2005 | Roundhill | |
| 2006/0241490 A1* | 10/2006 | Lazenby | A61B 8/4483 600/472 |
| 2010/0004539 A1* | 1/2010 | Chen | A61B 8/0825 600/445 |
| 2013/0281834 A1* | 10/2013 | Tashiro | A61B 8/0841 600/424 |
| 2014/0044325 A1* | 2/2014 | Ma | G06T 19/00 382/128 |
| 2017/0090571 A1* | 3/2017 | Bjaerum | G06F 3/016 |

\* cited by examiner

*Primary Examiner* — Shivang I Patel
(74) *Attorney, Agent, or Firm* — Anthony M. Del Zoppo, III; Daugherty & Del Zoppo Co., LPA

(57) ABSTRACT

An ultrasound focal zone display includes an image area for displaying an ultrasound image, a plurality of depth markers, the plurality of depth markers representative of a predetermined tissue depth of the displayed ultrasound image, a focus indicator representative of a maximum acoustic beam intensity of the displayed ultrasound image, and a focal zone extent representative of acoustic beam intensity values within a predetermined range below the maximum acoustic beam intensity value, the focus indicator being adjacent or overlapping the focal zone extent, the position of the focus indicator being asymmetrical relative to the focal zone extent.

20 Claims, 4 Drawing Sheets

ULTRASOUND FOCAL ZONE SYSTEM AND METHOD

CROSS REFERENCE TO RELATED APPLICATIONS

This application claims the benefit of U.S. provisional application Ser. No. 62/198,345 filed Jul. 29, 2015, which is incorporated herein by reference.

FIELD OF THE INVENTION

The invention relates generally to the field of medical diagnostic ultrasound systems and methods, and in particular to the display of ultrasound images.

BACKGROUND

The invention relates medical diagnostic ultrasound imaging systems, and, more particularly, to a diagnostic ultrasound imaging system displaying an ultrasound image.

SUMMARY

Aspects of the application address the above matters, and others.

The invention relates medical diagnostic ultrasound imaging systems, and, more particularly, to a diagnostic ultrasound imaging system displaying an ultrasound image.

In one aspect, an ultrasound focal zone display includes an image area for displaying an ultrasound image, a plurality of depth markers, the plurality of depth markers representative of a predetermined tissue depth of the displayed ultrasound image, a focus indicator representative of a maximum acoustic beam intensity of the displayed ultrasound image, and a focal zone extent representative of acoustic beam intensity values within a predetermined range below the maximum acoustic beam intensity value, the focus indicator being adjacent or overlapping the focal zone extent, the position of the focus indicator being asymmetrical relative to the focal zone extent.

In another aspect, a method includes displaying an ultrasound image, display a focal zone extent for the displayed image, and displaying a focus indicator for the displayed image, wherein the focus indicator is displayed in an asymmetrical position relative to the focal zone extent.

In another aspect, a method includes displaying a focal zone extent on a display, and displaying the ultrasound image on the display whereby a focus indicator for the image is displayed in an asymmetrical position relative to the focal zone extent.

In another aspect, a method includes displaying an ultrasound image on a display such that a focus indicator is not symmetrical relative to a focal zone extent, the focus indicator representative of a maximum acoustic beam intensity of the ultrasound image, and the focal zone extent representative of acoustic beam intensity values within a predetermined range below the maximum acoustic beam intensity value.

In another aspect, an ultrasound imaging system comprises an array of transducer elements, an electronic device, an interface configured to route an output single of the array of transducer elements to the electronic device, which processes the signal and generates an image signal, and a display device. The electronic device displays the image signal in a display/image area of the display device as an ultrasound image, depth markers corresponding to depths of tissue represented in the ultrasound image, focus indicia identifying a depth for an acoustic beam intensity of interest, and a focal zone extent with start and end point values based on the acoustic beam intensity of interest.

In another aspect, a method comprises receiving echoes with an array of transducer elements, generating, with the array of transducer elements, an electrical signal indicative of the received echoes, constructing an ultrasound image, from the electrical signal, in a display/image area of a display device, constructing a depth bar next to the ultrasound image in a direction representing depth in the ultrasound image, constructing focus indicia identifying a depth for a maximum acoustic beam intensity of the ultrasound image with respect to the depth bar, determining start and ends points for a graphical focal zone extent based on the maximum acoustic beam intensity, and displaying the graphical focal zone extent with respect to the depth bar.

In another aspect, a non-transitory computer readable medium is encoded with computer executable instructions which when executed by a processor of a computer causers the processor to: render an ultrasound image in a display/image area of a display device, create a depth bar next to the ultrasound image, create focus indicia identifying a depth for an acoustic beam intensity of the ultrasound image with respect to the depth bar, compute start and end points for a graphical focal zone extent based on the acoustic beam intensity, and display the graphical focal zone extent in conjunction with the focus indicia and the depth bar.

Those skilled in the art will recognize still other aspects of the present application upon reading and understanding the attached description.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF EXEMPLARY EMBODIMENTS

Figure 1:
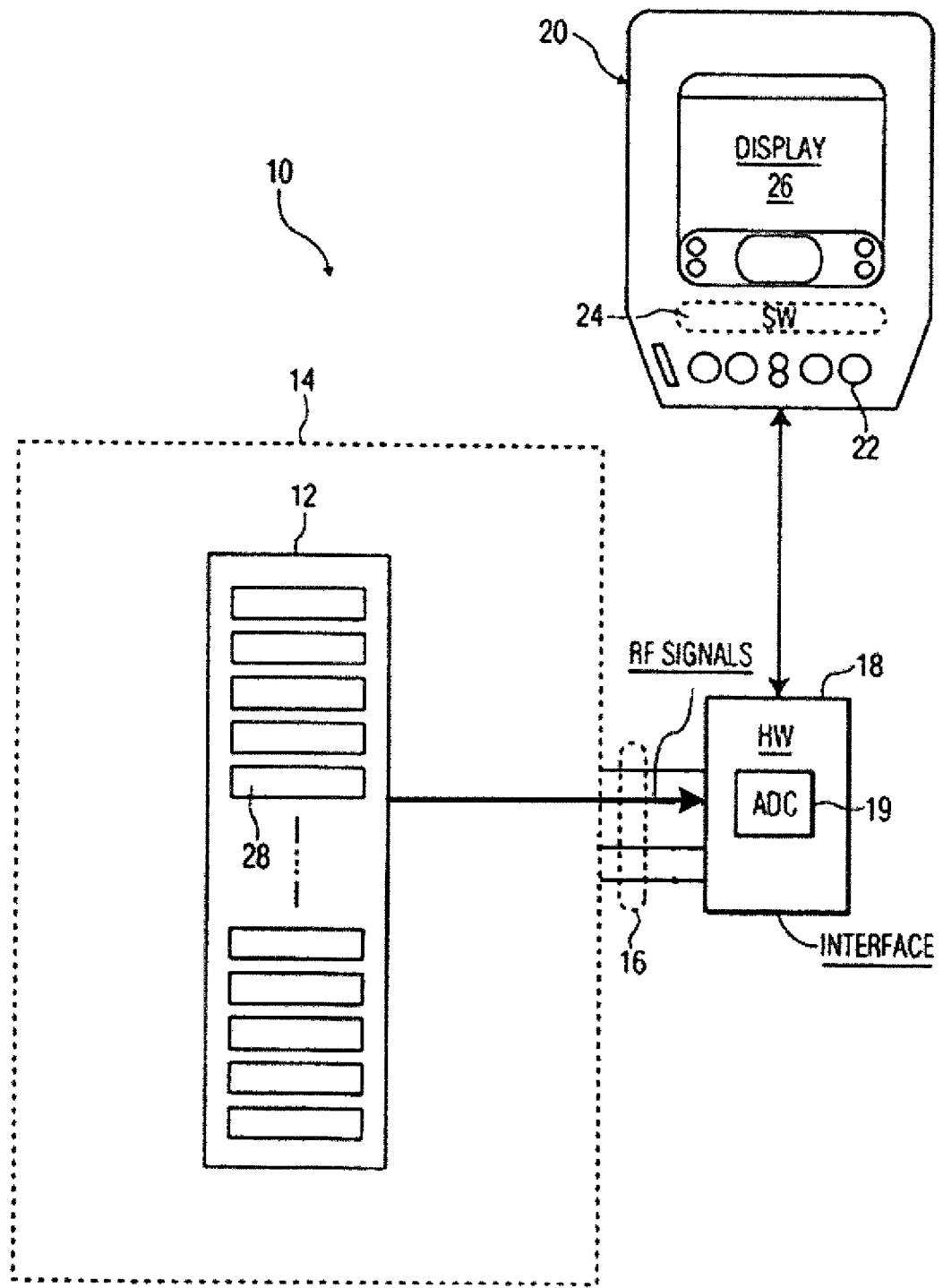
FIG. 1 shows an ultrasound imaging systems/methods

The following is a detailed description of the embodiments of the invention, reference being made to the drawings in which the same reference numerals identify the same elements of structure in each of the several figures.

Ultrasound imaging systems/methods are well known. See for example U.S. Pat. No. 6,705,995 (Poland) and U.S. Pat. No. 5,370,120 (Oppelt), both incorporated herein in their entirety.

Phased array ultrasonic imaging systems have been used to produce real-time images of internal portions of the human body. Such imaging systems include a multiple channel transmit beamformer and a multiple channel receive beamformer either coupled to a single array of ultrasonic transducers using a transmit/receive switch, or coupled separately to a transmit transducer array and a receive transducer array. The transmit beamformer generates timed electrical pulses and applies them to the individual transducer elements in a predetermined timing sequence. The transducers respond to the electrical pulses and emit corresponding pressure waves, which are phased to form a transmit beam that propagates in a predetermined direction from the transducer array.

As the transmit beam passes through the body, a portion of the acoustic energy is scattered back toward the transducer array from tissue structures having different acoustic characteristics. An array of receive transducers (which may be the same as the transmit array) converts the pressure pulses into the corresponding electrical pulses. Due to different distances, the ultrasonic energy scattered from a tissue structure, arrives back at the individual transducers at different times. Each transducer produces an electrical signal that is amplified and provided to one processing channel of the receive beamformer. The receive beamformer has a plurality of processing channels with compensating delay elements connected to a summing element. The system selects a delay value for each channel to collect echoes scattered from a selected point.

Consequently, when the delayed signals are summed, a strong signal is produced from signals corresponding to the selected point, but signals arriving from other points, corresponding to different times, have different phase relationships and thus destructively interfere. The relative delays of the compensating delay elements control the orientation of the receive beam with respect to the transducer array. By varying the delays during reception of echoes from a given transmit event, the receive beamformer can steer the receive beam to have a desired direction and can dynamically focus over a range of depths.

To collect imaging data, the transmit beamformer directs the transducer array to emit ultrasound beams along multiple transmit scan lines distributed over a desired scan pattern. For each transmit beam, the receive transducer array connected to the receive beamformer synthesizes one or several receive beams having selected orientations. The transmit and receive beams form a round-trip beam (i.e., "center of mass" beam) that is generated over a predetermined angular spacing to create a wedge-shaped acoustic image or is generated over a predetermined linear spacing to create a parallelogram-shaped acoustic image. Arbitrary combinations of the aforementioned patterns can be used to create more complex scanned image shapes, with arbitrary density of acoustic sampling.

A one-dimensional array may have up to several hundred elements. These elements are typically connected to a system with 128 channels of processing electronics. The receive beamformer within these channels uses digital signal processing involving an A/D converter and digital circuitry.

Referring to FIG. 1, a phased array ultrasonic imaging system 10 includes an array of transducer elements 28 located in a transducer handle 14. Transducer handle 14 operatively couples via a transducer cable 16 and a transducer interface 18 to an electronics unit 20. Interface 18 may include, for example, an analog to digital converter 19 (ADC) for converting analog signal to respective digital signals, as well as other circuitry. Electronics unit 20 includes a control panel 22, operating and application software 24, and provides imaging signals to display 26. Software 24 includes components for image detection and scan conversion. Image detection preferably includes the steps or RE filtering, mixing, analytic echo envelope detection, log-ging, and further smoothing. Scan conversion converts the echo data from the format of the scanned acoustic lines to the preferably Cartesian format of display 26.

Transducer array 12 can include several hundred transducer elements 28 arranged as a large one-dimensional array, phased array (PA), linear array (LA) or curved linear array (CLA) according to the requirements for a particular ultrasound imaging system. In addition, transducer array 12 may have the transducer elements arranged into separate transmit and receive arrays distributed along the one-dimensional array. Alternatively, the transducer transmit and receive elements may be distributed over a semi-random pattern along the one-dimensional array.

The quality of an image obtained using a diagnostic ultrasound imaging system is a function of numerous acquisition and/or display parameters and/or selected operating modes. These parameters are generally adjusted and operating modes selected by a sonographer or other healthcare professional prior to and during an ultrasound examination to optimize an image displayed by the system for the desired diagnosis. Acquisition parameters include transmit parameters like transmit frequency, transmit power, transmit beam location and transmit depth as well as receive parameters like the number of scan lines processed, the number of scan lines interpolated between transmit lines, and aberration correction values. Display parameters include, for example, the dynamic range, resolution, contrast and persistence of a displayed image. Operating modes that may be selected during an ultrasound examination include, for example, spatial compounding, harmonic imaging, 2-dimensional or 3-dimensional imaging and Doppler imaging. All of these display and acquisition parameters and operating modes as well as other similar parameters and operating modes can collectively be referred to as the "settings" of an ultrasound imaging system. See for example, U.S. Pat. No. 6,951,543 (Roundhill), incorporated herein in its entirety.

Applicants have developed a method to display an ultrasound medical image. There is provided a user interface, which allows the user/technician to view the ultrasound image.

Figure 2:
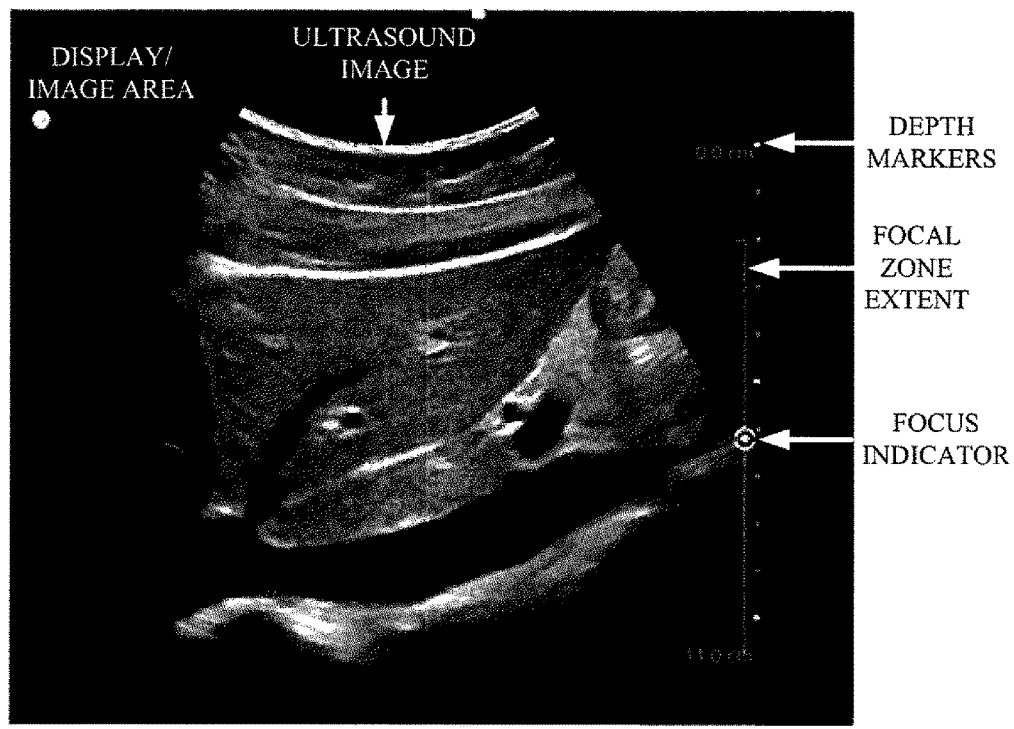
FIG. 2 shows an ultrasound image display in accordance with the present invention.

Referring to FIG. 2, there is shown an ultrasound image having an ultrasound focal zone display. The display includes an image area and a setting/marker/parameter/measurement/ruler area. The image area displays an ultrasound image. The ruler area indicates data/dimensional information related/associated with the displayed image.

In a preferred arrangement, the ruler area is positioned to be viewable simultaneously with the image area. As such, the ruler area can be near/adjacent and/or abutting and/or overlapping (all or partially) the image area.

The ruler area includes at least one (preferably a plurality) depth marker. FIG. 2 illustrates a plurality of depth markers, each illustrated as a horizontal dash, though other shapes could be employed (such as a +, =, dot, triangle, symbol, character, or the like). The plurality is vertically displayed adjacent the image area. The depth markers are representative of a predetermined tissue depth of the displayed ultrasound image. A value can be noted adjacent the depth marker. As illustrated in FIG. 2, the depth markers range from 0 cm to 11 cm.

The ruler area further includes a focus indicator representative of a maximum acoustic beam intensity of the displayed ultrasound image. In FIG. 2, this is illustrated as a circle, but could be of another shape – such as a +, square, dot, triangle, symbol, or the like.

The ruler area further includes a focal zone extent representative of acoustic beam intensity values within a predetermined range below the maximum acoustic beam intensity value (e.g., spatial region where intensity is about 10% below the maximum). In FIG. 2, the focal zone extent is illustrated as a vertical line, though other shapes could be employed, such as a dashed line, dotted line, or the like.

The focus indicator can near/adjacent and/or abutting and/or overlapping (all or partially) the focal zone extent. In FIG. 2, the focus indicator is at least partially overlapping the focal zone extent.

The depth markers can be near/adjacent and/or abutting and/or overlapping (all or partially) the focal zone extent. In FIG. 2, the depth markers are adjacent the focal zone extent.

The position of the focus indicator is asymmetrical relative to the focal zone extent. That is, the ultrasound image is displayed in the display area such that the focus indicator is asymmetrical relative to the focal zone extent. That is, the ultrasound image is displayed such that the focus indicator is not at the center/midway/midpoint/halfway position of the focal zone extent. This is motivated by the acoustic physics calculations that demonstrate that the acoustic intensity is asymmetric on either side of the maximum intensity location.

In a preferred arrangement, as the ultrasound image changes during the ultrasound procedure, any new image would be displayed in this same manner, that is, such that the focus indicator is asymmetrical relative to the focal zone extent.

As such, there is described an ultrasound focal zone display, comprising: an image area for displaying an ultrasound image; a plurality of depth markers (illustrated in FIG. 2 as dashes vertically displayed adjacent the image area), the plurality of depth markers representative of a predetermined tissue depth of the displayed ultrasound image; a focus indicator (illustrated in FIG. 2 as a circle) representative of a maximum acoustic beam intensity of the displayed ultrasound image; and a focal zone extent (illustrated in FIG. 2 as a vertical line) representative of acoustic beam intensity values within a predetermined range below the maximum acoustic beam intensity value, the focus indicator being adjacent or overlapping the focal zone extent, the position of the focus indicator (i.e., the circle) being located in a position asymmetrical relative to the focal zone extent (i.e., the line).

Figure 3:
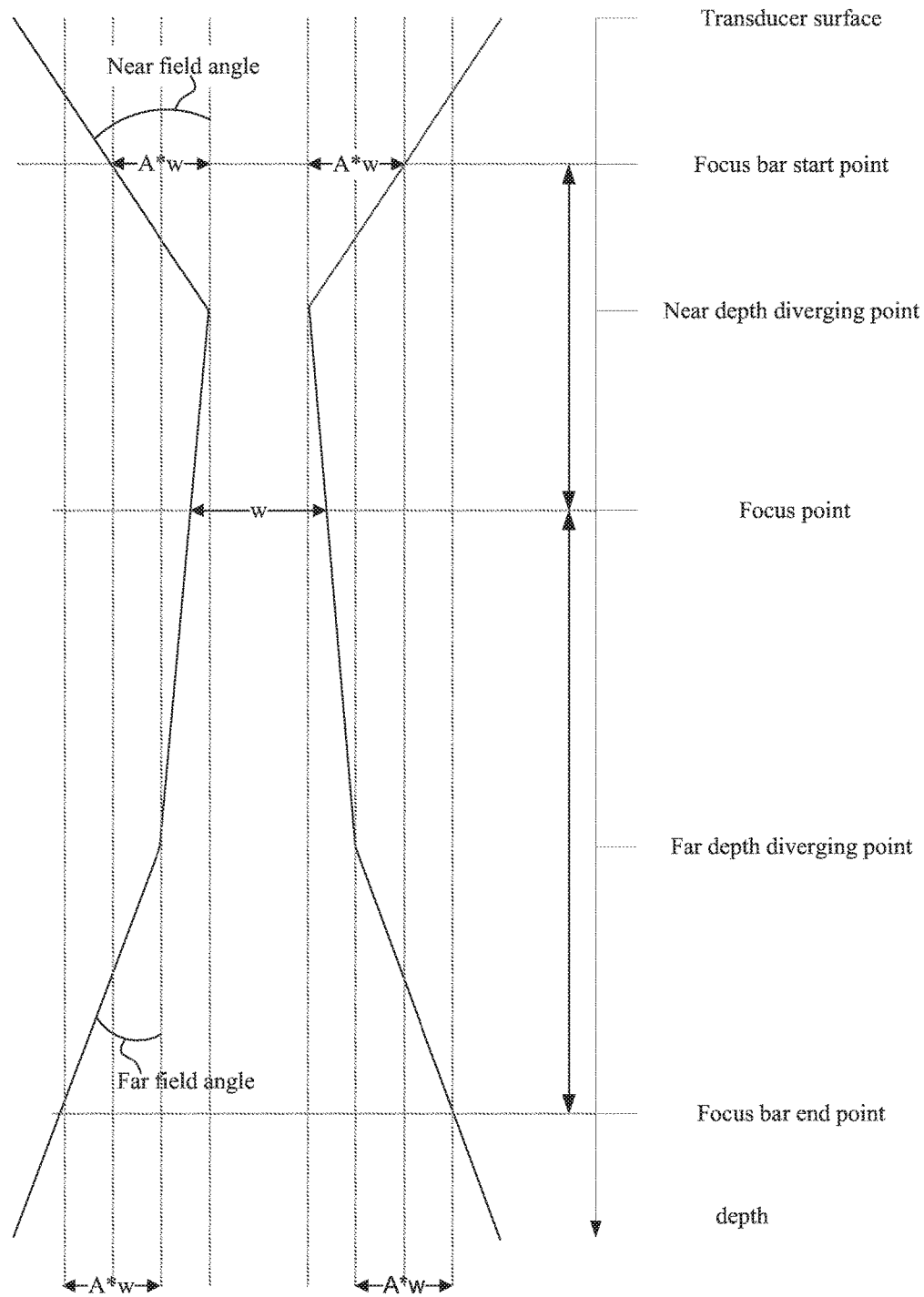
FIG. 3 shows an example beam shape model.

As described herein, the focus indicator is asymmetrical relative to the focal zone extent. FIG. 3 shows an example beam shape model, which can be used to determine a location of a focus bar start point, and a focus bar end point. In this example, the focus point is determined via an input indicating a user identified primary depth of interest. The ultrasonic imaging system 10 uses this input to select a pre-measured focus point that has a focusing depth close to the user-specified depth of interest.

The ultrasonic imaging system 10 determines a beam width ("w") at that pre-measured focus point. In one instance, the ultrasonic imaging system 10 determines the beam width ("w") as a product of the F# and wavelength (w=F#·λ). Other approaches for determining the beam width are also contemplated herein. A parameter A can be used to tune the length of the focus bar to what is a visual point of slight degradation of the focusing. An example of a value of the parameter A is 1. The ultrasonic imaging system 10 determines the focus bar start and end points based on an intensity of the pressure, e.g., utilizes a piece-wise linear approximation to determine the beam shape.

Figure 4:
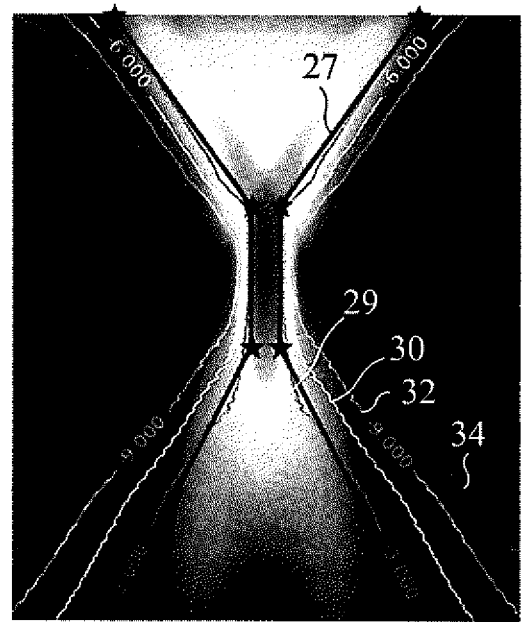
FIG. 4 shows a 2-D plot of pressure intensity of a focused beam.
Figure 5:
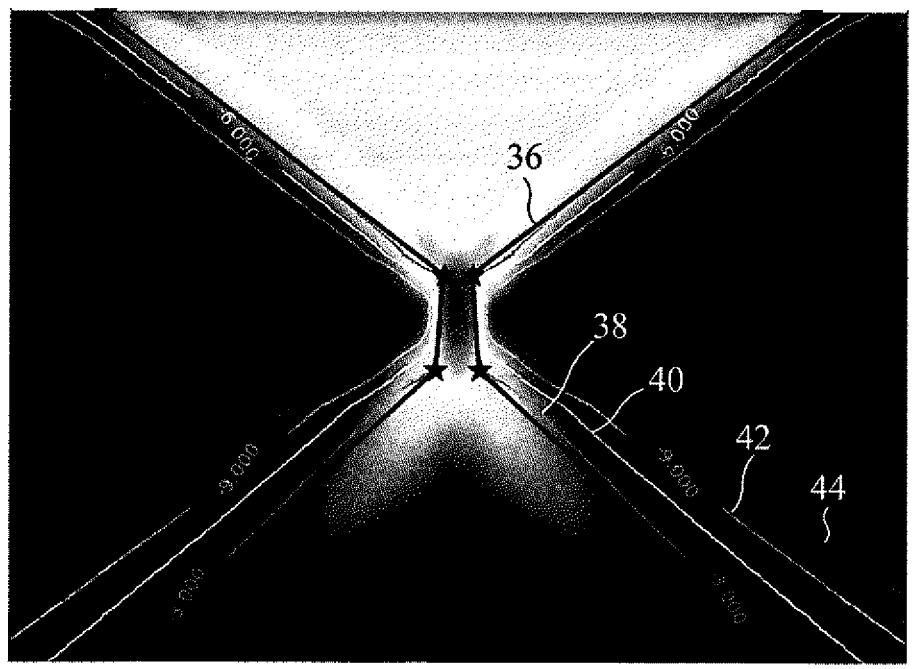
FIG. 5 shows another 2-D plot of pressure intensity of a focused beam.

FIGS. 4 and 5 show examples of this. FIG. 4 and FIG. 5 show 2-D plots of pressure intensity of a focused beam obtained, e.g., from hydrophone measurements or from accurate pressure field simulations. The units of both a vertical and a horizontal axis of the 2-D plot are meters, and the vertical axis is the scanning depth. The transducer properties and the scanning parameters such as focusing depth determine the pressure intensity. In FIG. 4, an approximated beam shape 27 is a result of a piece-wise linear approximation. Contour plots 29, 30, 32 and 34 show where the intensity has dropped 3, 6, 9 and 12 dB, respectively. In FIG. 5, an approximated beam shape 36 is a result of a piece-wise linear approximation. Contour plots 38, 40, 42 and 44 show where the intensity has dropped 3, 6, 9 and 12 dB, respectively.

Returning to FIG. 3, from the piece-wise linear approximations of FIGS. 4 and 5, the ultrasonic imaging system 10 determines locations of a near depth diverging point and a far depth diverging point. The ultrasonic imaging system 10 can also determine other parameters such as a near field angle, a far field angle and/or other parameters. These parameters may be a result of a fitting process using the hydrophone measurements or the pressure field simulations, or they may be computed by the ultrasonic imaging system 10 from the transducer parameters and the beamforming parameters.

Figure 6:
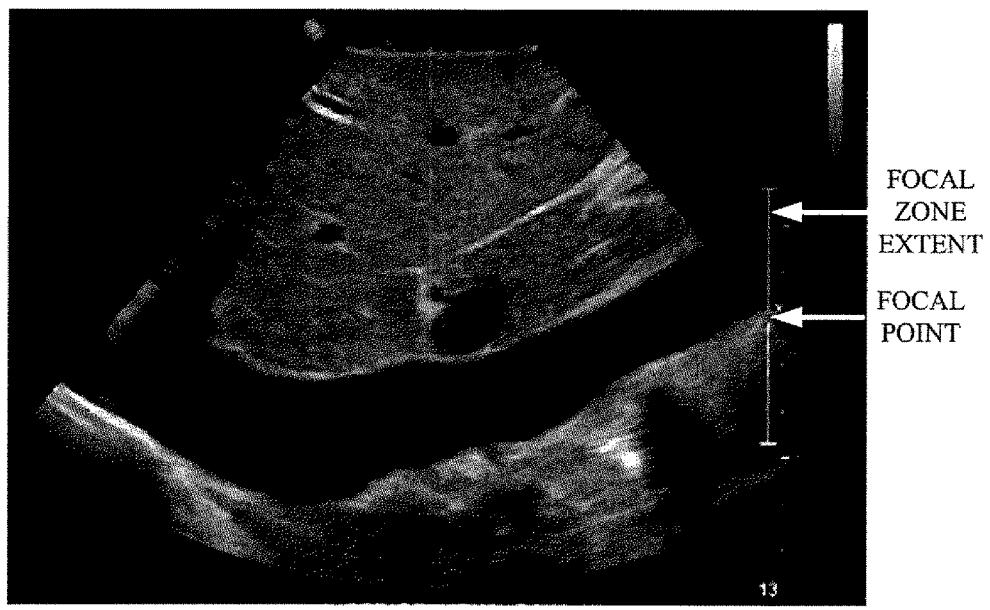
FIG. 6 shows a prior art image with a focal zone symmetrically disposed around a user requested focal point.

As described herein, the ultrasonic imaging system 10 computes a focal zone extent that is representative of the acoustic beam intensity value. In this example, the ultrasonic imaging system 10 determines where a width of the beam is N times w (N·w) for both the near and far fields, where N is a pre-determined scaling factor inversely corresponding to the acoustic beam intensity value. In one example, N=2. The ultrasonic imaging system 10 determines the focus bar start point at the width in the near field and the focus bar end point at the width in the far field. The focus bar start and/or end points can be manually adjusted by a user. FIG. 6 shows a prior art example with a user defined focal zone extent that is symmetric about a focal point.

For instances in which there are multiple focal zones, the ultrasonic imaging system 10 can determines the focus bar start point and/or the focus bar end point based on one of the multiple focal zones or on two or more of the multiple focal zones. For the latter, the focus bar start point can be set to the focus bar start point closest to the transducer surface, and the focus bar end point can be set to the focus bar end point farthest away from the transducer surface. In this instance, the resulting focal zone extent is a combination of the focal zone extents of the multiple focal zones that concurrently covers more than one focal zone.

The present invention can be a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention

The invention claimed is:

1. An ultrasound focal zone display, comprising:
    an image area for displaying a two-dimensional ultrasound image; and
    a ruler along an entirety of a depth of the two-dimensional ultrasound image, the ruler including:
        a plurality of depth markers, each of the plurality of depth markers representative of a different predetermined tissue depth of the displayed ultrasound image;
        a graphical focus indicator disposed on the ruler at a location that visually indicates a focusing depth representative of a maximum acoustic beam intensity of the displayed ultrasound image; and
        a graphical focal zone extent line with a first end representing a focus start depth corresponding to a first acoustic beam intensity value within a first predetermined range below the maximum acoustic beam intensity value and a second ends representing a focus end depth corresponding to a second different acoustic beam intensity values within a second predetermined range below the maximum acoustic beam intensity value,
        the graphical focus indicator being adjacent or overlapping the graphical focal zone extent line at the focusing depth, the position of the graphical focus indicator being asymmetrical relative to the first and second ends of the graphical focal zone extent line, the graphical focal zone extent line being adjacent to the plurality of depth markers, and the graphical focal zone extent line extending less than the entirety of the depth.

2. The display of claim 1, wherein the plurality of depth markers are dashes vertically displayed adjacent the image area.

3. A method comprising:
    displaying an ultrasound image including a depth and a width;
    displaying a focal zone extent line, which includes first and second opposing ends, on the displayed image along only a sub-portion of the depth of the displayed image, which is less than an entire depth of the displayed image; and
    displaying a focus indicator on the focal zone extent line, in an asymmetrical position relative to the first and second ends of the focal zone extent line, wherein the focus indicator visually indicates a location along the depth corresponding to a maximum acoustic beam intensity of the displayed ultrasound image.

4. A method of displaying an ultrasound image comprising:
    displaying a focal zone extent on a display adjacent to a plurality of depth markers, wherein the focal zone extent is next to only a sub-set of the plurality of depth markers that fall within a predetermined range below a maximum acoustic beam intensity value, and the sub-set includes less than all of the plurality of depth markers; and
    displaying the ultrasound image on the display whereby a focus indicator for the image is displayed on the focal zone extent in an asymmetrical position relative to the focal zone extent.

5. A method, comprising displaying an ultrasound image on a display such that a focus indicator is not symmetrical relative to a focal zone extent, the focus indicator representative of a maximum acoustic beam intensity of the ultrasound image, the focal zone extent representative of acoustic beam intensity values within a predetermined range below the maximum acoustic beam intensity value, and the focal zone extent is less than an entirety of a depth of the ultrasound image.

6. An ultrasound imaging system, comprising:
    an array of transducer elements;
    an electronic device;
    an interface configured to route an output single of the array of transducer elements to the electronic device, which processes the signal and generates an image signal; and
    a display device, wherein the electronic device displays the image signal in a display/image area of the display device as an ultrasound image, depth markers corresponding to depths of tissue represented in the ultrasound image, focus indicia at a depth marker of the depth markers corresponding to a depth for an acoustic beam intensity of interest, and a focal zone extent with start and end point values based on the acoustic beam intensity of interest.

7. The system of claim 6, wherein the acoustic beam intensity of interest is a maximum acoustic beam intensity of the ultrasound image, and at least one of the end point value or the start point value is a function of a value of the acoustic beam intensity of interest.

8. The system of claim 6, wherein the focus indicia includes a graphic that represents a user-identified position for the focus indicator.

9. The system of claim 7, wherein at least one of the end point value or the start point value is a function of the acoustic beam intensity profile.

10. The system of claim 6, wherein the focus indicia is located asymmetrically between the start and end point.

11. A method, comprising:
    receiving echoes with an array of transducer elements;
    generating, with the array of transducer elements, an electrical signal indicative of the received echoes;
    constructing an ultrasound image, from the electrical signal, in a display/image area of a display device;
    constructing a depth bar next to the ultrasound image in a direction representing depth in the ultrasound image;
    constructing focus indicia graphically at a depth on the depth bar for a maximum acoustic beam intensity of the ultrasound image;
    determining start and ends points for a graphical focal zone extent based on the maximum acoustic beam intensity; and
    displaying the graphical focal zone extent with respect to the depth bar.

12. The method of claim 11, further comprising:
    computing a beam width corresponding to the maximum acoustic beam intensity;
    identifying a beam width in a far field based on a pre-determined scaling factor multiplied by the beam width for the maximum acoustic beam intensity; and
    determining a value of the end point based on the beam width in the far field.

13. The method of claim 12, further comprising:
    receiving an input indicative of a user change in the value of the end point; and
    updating the displayed the graphical focal zone extent with the change in the value of the end point.

14. The method of claim 12, further comprising:
identifying a beam width in a near field of view based on the pre-determined scaling factor multiplied by the beam width for the maximum acoustic beam intensity; and
determining a value of the start point based on the beam width in the near field.

15. The method of claim 14, further comprising:
receiving an input indicative of a change in value of the start point; and
updating the displayed the graphical focal zone extent with the change in the value of the start point.

16. The method of claim 11, wherein the focus indicia is first focus indicia corresponding to a first focal zone, and further comprising:
determining one or more other start and end points for one or more other focal zones; and
determining a combined graphical focal zone extent based on the start and end points and the other start and end points.

17. The method of claim 16, wherein an end point of the combined graphical focal zone extent corresponds to an end point farthest from the array of transducer elements.

18. The method of claim 17, wherein a start point of the combined graphical focal zone extent corresponds to a start point closest to the array of transducer elements.

19. The method of claim 11, wherein the focus indicia is asymmetrically between the first and the second end points.

20. A non-transitory computer readable medium encoded with computer executable instructions which when executed by a processor of a computer causers the processor to:
render an ultrasound image in a display/image area of a display device;
create a depth bar next to the ultrasound image;
create focus indicia graphically at a depth on the depth bar for an acoustic beam intensity of the ultrasound image;
compute start and end points for a graphical focal zone extent based on the acoustic beam intensity; and
display the graphical focal zone extent in conjunction with the focus indicia and the depth bar.

* * * * *